US009636076B2

(12) United States Patent
Fujisawa et al.

(10) Patent No.: US 9,636,076 B2
(45) Date of Patent: *May 2, 2017

(54) X-RAY CT APPARATUS AND IMAGE PROCESSING METHOD

(71) Applicant: TOSHIBA MEDICAL SYSTEMS CORPORATION, Otawara (JP)

(72) Inventors: Yasuko Fujisawa, Otawara (JP); Shinsuke Tsukagoshi, Nasushiobara (JP); Shinji Muramatsu, Otawara (JP); Takumi Ishizaka, Yaita (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/953,231

(22) Filed: Nov. 27, 2015

(65) Prior Publication Data

US 2016/0073994 A1 Mar. 17, 2016

Related U.S. Application Data

(63) Continuation-in-part of application No. 13/431,097, filed on Mar. 27, 2012, now Pat. No. 9,230,334.

(30) Foreign Application Priority Data

Mar. 29, 2011 (JP) ................................. 2011-072805

(51) Int. Cl.
*G06K 9/00* (2006.01)
*A61B 6/00* (2006.01)
(Continued)

(52) U.S. Cl.
CPC .......... *A61B 6/5217* (2013.01); *G06T 7/0016* (2013.01); *G06T 7/246* (2017.01);
(Continued)

(58) Field of Classification Search
None
See application file for complete search history.

(56) References Cited

U.S. PATENT DOCUMENTS 7,946,992 B2 5/2011 Umemura et al.
8,098,921 B2 1/2012 Matsumura
(Continued)

FOREIGN PATENT DOCUMENTS

EP 1 880 673 A1 1/2008
EP 1 980 210 A1 10/2008
JP 4861647 11/2011

OTHER PUBLICATIONS

European Office Action issued Sep. 9, 2014 in European Patent Application No. 12162302.9-1906.
(Continued)

*Primary Examiner* — Soo Jin Park
(74) *Attorney, Agent, or Firm* — Oblon, McClelland, Maier & Neustadt, L.L.P.

(57) ABSTRACT

An X-ray CT apparatus according to an embodiment includes an image processing circuit. The image processing circuit generates image data of an inside of a patient. The image processing circuit specifies a position of a tumor and a position of a surrounding site positioned in a surrounding of the tumor, from the generated pieces of image data. The image processing circuit calculates movement information related to movements of the tumor and the surrounding site, based on the specified positions of the tumor and the surrounding site. The image processing circuit calculates a relative relationship between the calculated movement information of the tumor and the surrounding site. The imaging processing circuit calculates a degree of coupling by which the tumor and the surrounding site are coupled, based on a
(Continued)

relative relationship between the movement information of the tumor and the surrounding site.

16 Claims, 8 Drawing Sheets

(51) Int. Cl.
    *G06T 7/00*             (2017.01)
    *G06T 7/246*           (2017.01)

(52) U.S. Cl.
    CPC ............... *G06T 2207/10081* (2013.01); *G06T 2207/30096* (2013.01)

(56) References Cited

U.S. PATENT DOCUMENTS

| | | |
|---|---|---|
| 8,457,379 B2 | 6/2013 | Tashiro et al. |
| 2004/0249287 A1 | 12/2004 | Kawashima et al. |
| 2008/0037851 A1 | 2/2008 | Takayama |
| 2009/0187422 A1 | 7/2009 | Kaus et al. |

OTHER PUBLICATIONS

Partial Search Report issued Sep. 4, 2013 in European Patent Application No. 12162302.9.

Eric D. Donnelly, et al., "Assessment of intrafraction mediastinal and hilar lymph node movement and comparison to lung tumor motion using four-dimensional ct", Int. J. Radiation Oncology Biol. Phys., vol. 69, No. 2, XP022243271, 2007, pp. 580-588.

Julien Dinkel, et al., "4D-MRI analysis of lung tumor motion in patients with hemidiaphragmatic paralysis", Radiotherapy dnd Oncology, vol. 91, No. 3, XP026129671, Jun. 1, 2009, pp. 449-454.

Eike Rietzel, et al., "Moving targets: detection and tracking of internal organ motion for treatment planning and patient set-up", Radiotherapy and Oncology, vol. 73, XP 005050405, Dec. 1. 2004, pp. S68-S72.

Gottlieb el al., "Investigation of respiration induced intra- and inter-fractional tumour motion using a standard Cone Beam CT", Acta Oncologica, 2010.

Hsiao et al., "Infra-tumor flow index can predict the malignant potential of breast tumor: dependent on age and volume", Ultrasound in Med. & Biol., 2008.

Weiss et al., "Tumor and normal tissue motion in the thorax during respiration: analysis of volumetric and positional variations using 4D CT", Int. J. Radiation Oncology Biol. Phys., 2007.

X-RAY CT APPARATUS AND IMAGE PROCESSING METHOD

CROSS-REFERENCE TO RELATED APPLICATIONS

This application is a continuation-in-part (CIP) of application Ser. No. 13/431,097 filed on Mar. 27, 2012, the entire content of which is hereby incorporated by reference in this application. This application is based upon and claims the benefit of priority from Japanese Patent Application No. 2011-072805, filed on Mar. 29, 2011; the entire contents of all of which are incorporated herein by reference.

FIELD

Embodiments described herein relate generally to an X-ray CT apparatus and an image processing method.

BACKGROUND

Methods for taking an image of the inside of an examined subject (hereinafter, "patient") by using an X-ray Computed Tomography (CT) apparatus are conventionally known. Examples of the known methods include a method for taking an image of the inside of a patient who is in a breath-holding state, an exhalation-period state, and an inhalation-period state. The examples of the known methods also include a method for taking an image of the inside of a patient in correspondence with a plurality of temporal phases, without specifying any respiratory state of the patient. Further, in recent years, X-ray CT apparatuses capable of imaging the inside of a patient over a large area and in a three-dimensional manner are also known. Thus, in some situations, an image of the inside of a patient is taken by using such X-ray CT apparatuses. These X-ray CT apparatuses are used for, for example, taking an image of a tumor inside a patient.

DETAILED DESCRIPTION

An X-ray CT apparatus according to an embodiment includes an image processing circuit. The image processing circuit generates pieces of image data of an inside of a patient corresponding to mutually-different temporal phases, based on X-rays having transmitted through the patient. The image processing circuit specifies a position of a tumor and a position of a surrounding site positioned in a surrounding of the tumor, from the generated pieces of image data of the inside of the patient corresponding to the mutually-different temporal phases. The image processing circuit calculates movement information related to movements of the tumor and the surrounding site, based on the specified positions of the tumor and the surrounding site. The image processing circuit calculates a relative relationship between the calculated movement information of the tumor and the surrounding site. The imaging processing circuit calculates a degree of coupling by which the tumor and the surrounding site are coupled, based on a relative relationship between the movement information of the tumor and the surrounding site.

First Embodiment

X-ray CT apparatuses are configured to radiate X-rays onto a patient from an X-ray tube and to cause a detector to detect the X-rays having transmitted through the patient, so as to reconstruct an X-ray CT image representing tissue morphological information on the inside of the patient. An X-ray CT apparatus according to a first embodiment is configured to reconstruct an X-ray CT image and to calculate a degree of infiltration (hereinafter, "infiltration degree") indicating a degree by which a tumor has infiltrated into a predetermined surrounding site, such as a lung field or the like. In the description of exemplary embodiments below, a "surrounding site" refers to an organ or the like positioned in the surrounding of a tumor. Examples of surrounding sites include a lung field, the pleura, a bronchus, the esophagus, the chest wall, the mediastinum, the diaphragm, and the like.

Figure 1:
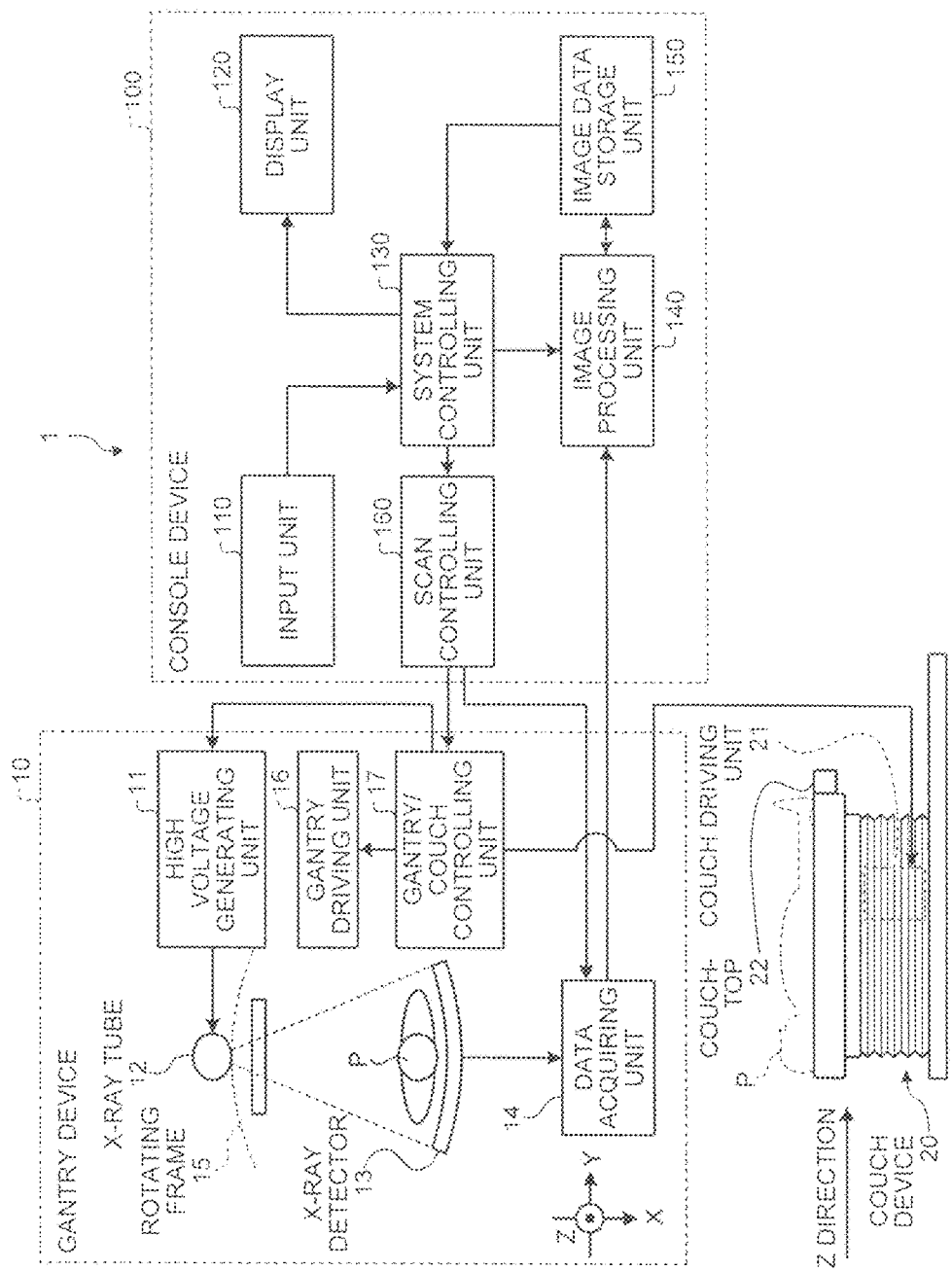
FIG. 1 is a diagram of an exemplary configuration of an X-ray CT apparatus according to a first embodiment.

A configuration of the X-ray CT apparatus according to the first embodiment will be explained, with reference to FIG. 1. FIG. 1 is a diagram of an exemplary configuration of an X-ray CT apparatus 1 according to the first embodiment. As shown in FIG. 1, the X-ray CT apparatus 1 according to the first embodiment includes a gantry device 10, a couch device 20, and a console device 100.

The gantry device is configured to radiate X-rays onto a patient P, to detect the X-rays having transmitted through the patient P, and to output the detection result to the console device 100. The gantry device 10 includes a high voltage generating unit 11, an X-ray tube 12, an X-ray detector 13, a data acquiring unit 14, a rotating frame 15, a gantry driving unit 16, and a gantry/couch controlling unit 17.

Under the control of the gantry/couch controlling unit 17, the high voltage generating unit 11 supplies a high voltage to the X-ray tube 12. The X-ray tube 12 is a vacuum tube configured to generate X-rays by using the high voltage supplied from the high voltage generating unit 11. The X-ray tube 12 radiates the X-rays onto the patient P, in conjunction with rotations of the rotating frame 15. In other words, the high voltage generating unit 11 is configured to adjust the amount of X-rays radiated onto the patient P, by adjusting a tube voltage and a tube electric current supplied to the X-ray tube 12.

The X-ray detector 13 is a two-dimensional array detector (an area detector) configured to detect X-rays having transmitted through the patient P. In the X-ray detector 13, a plurality of detecting-element rows each made up of X-ray detecting elements corresponding to a plurality of channels are arranged along a body-axis direction of the patient P (i.e., a Z-axis direction shown in FIG. 1). More specifically, the X-ray detector 13 according to the first embodiment includes X-ray detecting elements arranged in a large number of rows such as 320 rows, along the body-axis direction of the patient P. The X-ray detector 13 is configured to be able to detect the X-rays having transmitted through the patient P over a large area such as, for example, an area including the lung and the heart of the patient P.

The data acquiring unit 14 is configured to generate projection data by using the X-rays detected by the X-ray detector 13 and to transmit the generated projection data to an image processing unit 140 included in the console device 100. The rotating frame 15 is an annular frame that continuously rotates at a high speed, while being centered on the patient P. The X-ray tube 12 and the X-ray detector 13 are positioned so as to oppose each other.

Under the control of the gantry/couch controlling unit 17, the gantry driving unit 16 drives a gantry. More specifically, the gantry driving unit 16 is configured to cause the rotating frame 15 to continuously rotate at a high speed with the drive of a motor and to cause the X-ray tube 12 and the X-ray detector 13 to continuously rotate on a circular track centered on the patient P. Under the control of a scan controlling unit 160 (explained later), the gantry/couch controlling unit 17 controls the high voltage generating unit 11, the gantry driving unit 16, and a couch driving unit 21.

In the first embodiment, by using the X-ray detector 13 configured with the two-dimensional array detector (the area detector), a conventional scanning process, which is to scan the patient P along the circular track by rotating the rotating frame 15 while the position of the patient P is fixed, is performed in correspondence with a plurality of temporal phases. In other words, the data acquiring unit 14 acquires a plurality of pieces of three-dimensional projection data corresponding to the mutually-different temporal phases resulting from the scanning process, by using the X-rays detected by the X-ray detector 13 and transmits the acquired three-dimensional projection data to the image processing unit 140.

The couch device 20 is a platform on which the patient P who serves as an image taking target is placed and includes the couch driving unit 21 and a couchtop 22. Under the control of the gantry/couch controlling unit 17, the couch driving unit 21 causes the couchtop 22 to continuously reciprocate along the body-axis direction of the patient P, with the drive of a motor. The couchtop 22 is a plate on which the patient P is placed.

The console device 100 is configured to receive an operation performed by an operator on the X-ray CT apparatus 1 and to reconstruct an X-ray CT image from the projection data acquired by the gantry device 10. More specifically, the console device 100 includes: an input unit 110, a display unit 120, a system controlling unit 130, the image processing unit 140, an image data storage unit 150, and the scan controlling unit 160.

The input unit 110 includes a mouse, a keyboard, and the like used by the operator of the X-ray CT apparatus 1 for inputting various types of instructions and various types of settings. The input unit 110 is configured to transfer information about the instructions and the settings received from the operator to the system controlling unit 130. For example, the input unit 110 receives an operation from the operator indicating that an infiltration degree of a tumor should be calculated and an operation to input a reconstruction condition used for reconstructing an X-ray CT image. The display unit 120 is a display monitor configured with, for example, a Liquid Crystal Display (LCD) device and is configured to display various types of information. For example, the display unit 120 displays an X-ray CT image stored in the image data storage unit 150 and Graphical User Interface (GUI) used for receiving various types of instructions from the operator.

By controlling the gantry device 10, the couch device 20, and the console device 100, the system controlling unit 130 controls the entirety of the X-ray CT apparatus 1. For example, the system controlling unit 130 controls the scan controlling unit 160 to acquire the three-dimensional projection data. Further, for example, the system controlling unit 130 controls the image processing unit 140 to reconstruct the X-ray CT image from the three-dimensional projection data.

The image processing unit 140 performs various types of processing processes on the three-dimensional projection data received from the data acquiring unit 14. More specifically, the image processing unit 140 performs a pre-processing process such as a sensitivity correcting process on the three-dimensional projection data received from the data acquiring unit 14. The image processing unit 140 further reconstructs a three-dimensional X-ray CT image (which, hereinafter, may be referred to as "volume data") by performing a back-projection process on the three-dimensional projection data on which the pre-processing process has been performed. After that, the image processing unit 140 stores the reconstructed volume data into the image data storage unit 150. Further, the image processing unit 140 is configured, for example, to generate an X-ray CT image having three-dimensionality by employing a Shaded Volume Rendering (SVR) method or the like and to generate a cross-sectional image on an arbitrary plane, so as to store the generated X-ray CT images into the image data storage unit 150.

Because the gantry device 10 according to the first embodiment is configured to perform the conventional scanning process in correspondence with the plurality of temporal phases, the image processing unit 140 performs the image reconstructing process described above on each of the pieces of three-dimensional projection data respectively corresponding to the temporal phases. Further, the image processing unit 140 according to the first embodiment not only generates the X-ray CT image, but also performs the process to calculate the infiltration degree of a tumor. The infiltration degree calculating process performed by the image processing unit 140 will be explained in detail later.

The image data storage unit 150 is configured to store therein the volume data, the X-ray CT images, and the like reconstructed by the image processing unit 140. The scan controlling unit 160 controls the gantry/couch controlling unit 17, according to a scan condition instructed by the system controlling unit 130.

As explained above, the X-ray CT apparatus 1 according to the first embodiment performs the process to calculate the infiltration degree of a tumor. This feature will be explained briefly. Movements of a "normal site (e.g., an organ)" are considered to be fundamentally different from movements of an "abnormal site (e.g., a tumor)". For example, the more a tumor, being malignant, has infiltrated into a predetermined surrounding site, the stiffer the tumor becomes and the more difficult it is for the tumor to come off the predetermined surrounding site. As a result, it becomes more difficult for such a tumor to move in synchronization with the movements of the other normal surrounding sites caused by respiratory movements and peristaltic movements. On the contrary, it is easier for a tumor having a low degree of infiltration into the predetermined surrounding site to come off the predetermined surrounding site and to move in synchronization with the movements of the other normal surrounding sites. In other words, it is possible to estimate the infiltration degree, which is the degree by which the tumor has infiltrated into the predetermined surrounding site, based on the movements of the tumor and the surrounding site.

The X-ray CT apparatus 1 according to the first embodiment calculates movement information related to movements of a tumor and movement information related to movements of a surrounding site positioned in a surrounding of the tumor, by analyzing the volume data generated in correspondence with the plurality of temporal phases and further calculates the infiltration degree of the tumor, based on a relationship between the two pieces of movement information. In the following sections, the infiltration degree calculating process performed by the X-ray CT apparatus 1 will be explained in detail, with reference to FIGS. 2 to 5.

Figure 2:
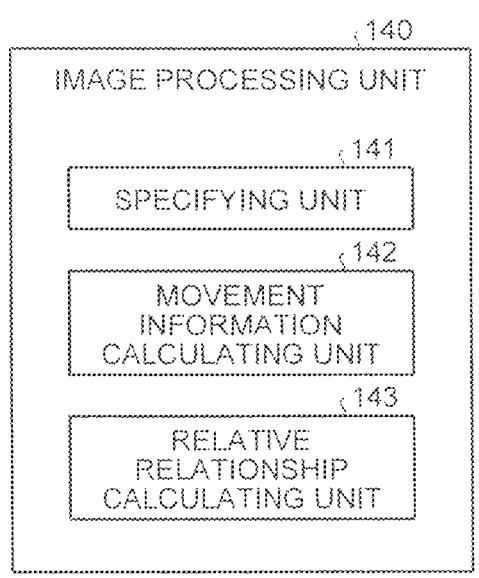
FIG. 2 is a diagram of an exemplary configuration of an image processing unit according to the first embodiment.

FIG. 2 is a diagram of an exemplary configuration of the image processing unit 140 according to the first embodiment. As shown in FIG. 2, the image processing unit 140 according to the first embodiment includes a specifying unit 141, a movement information calculating unit 142, and a relative relationship calculating unit 143. The processing unit that generates the volume data and the processing unit that generates an X-ray CT image for display purposes are omitted from FIG. 2.

The specifying unit 141 specifies the position of the tumor and the position of a surrounding site of the tumor within the volume data reconstructed by the image processing unit 140. The image processing unit 140 according to the first embodiment reconstructs the plurality of pieces of volume data corresponding to the mutually-different temporal phases. Thus, the specifying unit 141 performs the process of specifying the positions of the tumor and the surrounding site, for each of the pieces of volume data corresponding to the temporal phases.

More specifically, the specifying unit 141 extracts regions by performing a segmentation process while applying a region growing method used for extracting regions in which CT values are spatially consecutive or a pattern matching method that uses shape templates, to the pieces of volume data reconstructed by the image processing unit 140. Subsequently, the specifying unit 141 specifies the positions of the tumor and the surrounding site contained in the volume data, by applying a pattern matching method that uses shape templates of the tumor and the surrounding site or a method that uses profiles of brightness values of the tumor and the surrounding site, to the extracted regions.

The movement information calculating unit 142 calculates the movement information related to the movements of the tumor and the surrounding site, based on the positions of the tumor and the surrounding site specified by the specifying unit 141. The "movement information" indicates temporal changes and positional changes in the positions of the tumor and the organs. In the first embodiment, let us assume that the "movement information" indicates temporal changes in the relative distance from a predetermined reference point to the tumor or to a site such as an organ. The predetermined reference point is, for example, an arbitrary point within the volume data or a site or the like such as the diaphragm or a lung apex.

Next, the process performed by the movement information calculating unit 142 will be explained more specifically. The movement information calculating unit 142 first aligns positions of two pieces of volume data that correspond to consecutive temporal phases and were reconstructed by the image processing unit 140. In this situation, the movement information calculating unit 142 may align the positions of the entirety of the two pieces of volume data or may align the positions of the two pieces of volume data with respect to a predetermined reference point.

Subsequently, the movement information calculating unit 142 calculates motion vectors indicating movement directions and movement amounts of the tumor and the surrounding site, by comparing the two pieces of volume data, on which the position aligning process has been performed, with each other. In this situation, for each of the voxels in the volume data, the movement information calculating unit 142 calculates a motion vector of the voxel. For example, to calculate the movement direction and the movement amount of the tumor, the movement information calculating unit 142 calculates, for each of the voxels in the region representing the tumor within the volume data, the motion vector of the voxel, by comparing the two pieces of volume data with each other. Further, to calculate the movement direction and the movement amount of the surrounding site (e.g., the lung field), the movement information calculating unit 142 calculates, for each of the voxels in the region representing the surrounding site (e.g., the lung field) within the volume data, the motion vector of the voxel, by comparing the two pieces of volume data with each other. In this situation, the movement information calculating unit 142 is able to calculate the motion vector of each of the voxels, based on information obtained during the position aligning process such as tracking.

After that, the movement information calculating unit 142 decomposes the motion vector of each of the voxels into motion vectors corresponding to an x-axis direction, a y-axis direction, and a z-axis direction in an x-y-z coordinate system of the volume data. As a result, the movement information calculating unit 142 is able to obtain, for each of the voxels, the movement amounts in the x-axis direction, the y-axis direction, and the z-axis direction of the tumor and surrounding sites thereof. For example, if a focus is placed on the motion vector in the x-axis direction, the movement information calculating unit 142 is able to obtain a movement amount of a voxel having moved in the x-axis direction from the starting point to the ending point of the motion vector.

By using two pieces of volume data corresponding to consecutive temporal phases from among the plurality of pieces of volume data reconstructed by the image processing unit 140, the movement information calculating unit 142 performs the process of calculating the motion vectors in the x-axis direction, the y-axis direction, and the z-axis direction, for all of the plurality of pieces of volume data. Further, the movement information calculating unit 142 calculates a relative distance from the reference point to the voxel, for each of the x-, the y-, and the z-axis directions. The temporal changes in the relative distance can be considered as a periodic function, because the movements of the sites inside the human body occur due to respiratory movements and peristaltic movements. In the following sections, a "temporal change in the relative distance from the reference point to X" may be simply referred to as a "distance change of X".

Figure 3:
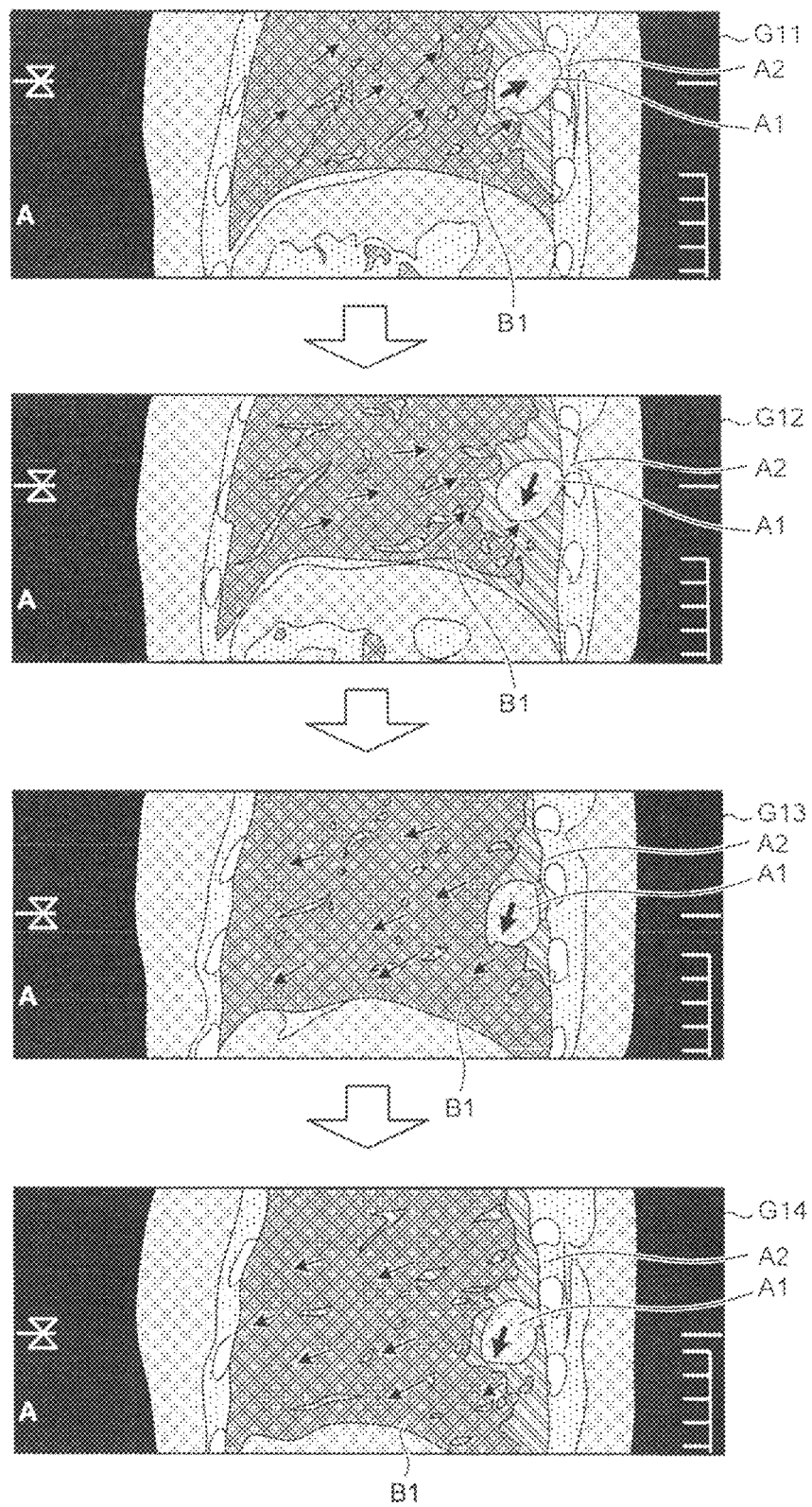
FIG. 3 depicts examples of images in a surrounding of a lung field.
Figure 4:
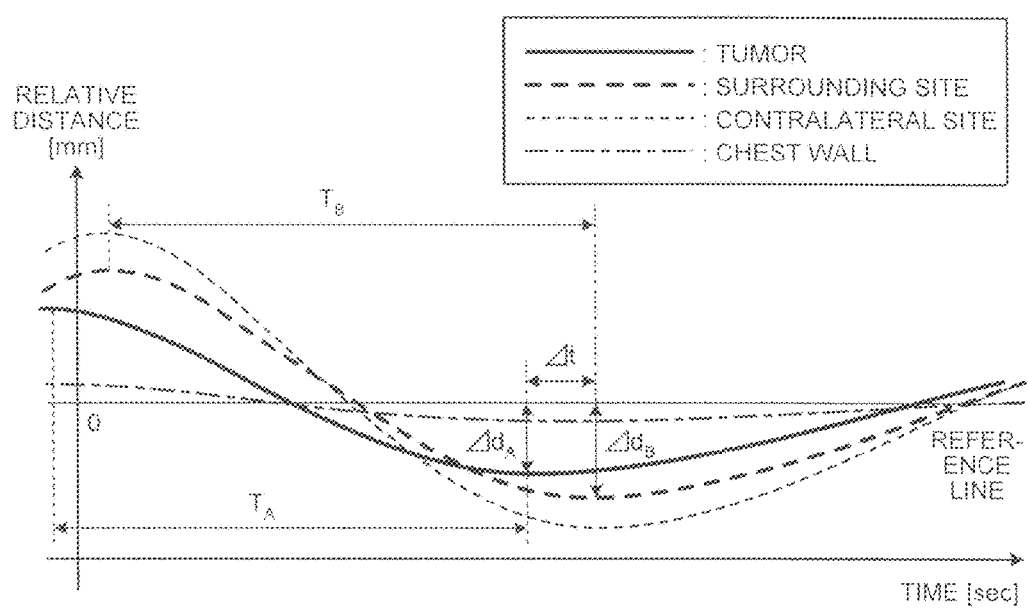
FIG. 4 is a chart of an example of movement information calculated by a movement information calculating unit.

The process performed by the movement information calculating unit 142 will be explained, with reference to FIGS. 3 and 4. FIG. 3 depicts examples of images in a surrounding of a lung field. FIG. 4 is a chart of an example of the movement information calculated by the movement information calculating unit 142.

In the examples depicted in FIG. 3, it is assumed that X-ray CT images G11, G12, G13, and G14 were sequentially taken in the stated order. In FIG. 3, cross-sectional images are shown, to keep the explanation simple. Further, in the examples depicted in FIG. 3, a tumor A1 has infiltrated into a predetermined surrounding site A2, whereas another surrounding site B1 positioned in a surrounding of the tumor A1 is a lung field.

As depicted in FIG. 3, it can be observed that the positions of the tumor A1 and the surrounding site B1 change, in the sequence of the X-ray CT images G11, G12, G13, and G14. As shown in FIG. 4, the movement information calculating unit 142 calculates, for each of the voxels, the distance changes of the tumor A1 and the surrounding site B1. Shown in FIG. 4 are the distance changes in the x-axis direction of predetermined voxels each representing a different one of the sites. Similarly, the movement information calculating unit 142 also calculates distance changes of each of the sites in the y-axis direction and the z-axis direction. Further, the movement information calculating unit 142 calculates the distance change not only with respect to the one voxel, but also with respect to each of the other voxels contained in each of the sites.

In the example shown in FIG. 4, the movement information calculating unit 142 calculates relative distances from a reference point (the reference line in FIG. 4), to a voxel representing the tumor (A1 in FIG. 3), to a voxel representing the lung field (B1 in FIG. 3) which is a surrounding site, to a voxel representing a contralateral site, and to a voxel representing the chest wall. Next, the term "contralateral site" will be explained. In a human body, some sites are substantially bilaterally symmetrical, like the lung fields (hereinafter, such a site may be referred to as a "symmetrical site"). When the surrounding site of the tumor is a symmetrical site, the "contralateral site" in FIG. 4 refers to the site positioned opposite to the surrounding site. For example, if the surrounding site shown in FIG. 4 is the right lung field, the left lung field is referred to as the "contralateral site". Such a "contralateral site" may be also used for calculating the infiltration degree, and this feature will be explained later.

As explained above, the movement information calculating unit 142 calculates the distance changes of the tumor, the surrounding site, the contralateral site, and the like for each of the voxels and for each of the x-, the y-, and the z-axis directions, by using the plurality of pieces of volume data corresponding to the mutually-different temporal phases.

In the example described above, the movement information calculating unit 142 calculates the distance change for each of the voxels. Those voxels may have an arbitrary size. For example, the movement information calculating unit 142 may calculate a distance change for each unit of "1×1×1 voxel" or may calculate a distance change for each unit of "4×4×4 voxels". Further, it is acceptable if the size of the unit made of voxels is determined by the operator or the like. Further, the movement information calculating unit 142 does not necessarily have to calculate the distance change for each of all the voxels representing the sites. For example, it is acceptable to configure the movement information calculating unit 142 to extract a voxel region containing a predetermined number of voxels from each of the sites and to calculate a distance change with respect to the extracted voxel regions.

Returning to the description of FIG. 2, the relative relationship calculating unit 143 calculates a relative relationship between the movement information of the tumor and the movement information of the surrounding site calculated by the movement information calculating unit 142. Further, the relative relationship calculating unit 143 calculates the infiltration degree indicating the degree by which the tumor has infiltrated into the surrounding site, based on the relative relationship.

More specifically, the relative relationship calculating unit 143 calculates the infiltration degree in such a manner that the smaller similarity there is between the periodical distance changes of the voxels representing the tumor and the periodical distance changes of the voxels representing the surrounding site (the surrounding site B1 in the example in FIG. 3) of the tumor, the higher is the infiltration degree indicating the degree by which the tumor has infiltrated into the predetermined surrounding site (e.g., the surrounding site A2 in the example in FIG. 3). In other words, the relative relationship calculating unit 143 calculates the infiltration degree in such a manner that the larger similarity there is between the periodical distance changes of the voxels representing the tumor and the periodical distance changes of the voxels representing the surrounding site (the surrounding site B1 in the example in FIG. 3) of the tumor, the lower is the infiltration degree indicating the degree by which the tumor has infiltrated into the predetermined surrounding site (e.g., the surrounding site A2 in the example in FIG. 3). The reason is that, as explained above, movements of a "normal site" are considered to be fundamentally different from movements of an "abnormal site (e.g., a tumor)". Thus, the more the tumor has infiltrated into the predetermined surrounding site (the surrounding site A2 in the example in FIG. 3), the smaller similarity there is between the periodical distance changes of the tumor and the normal surrounding site (the surrounding site B1 in the example in FIG. 3).

An example of the process performed by the relative relationship calculating unit 143 will be explained, with reference to FIG. 4. When the movement information calculating unit 142 has calculated the distance changes as shown in FIG. 4, the relative relationship calculating unit 143 calculates amplitudes, cycles, and the like, with respect to the periodical distance changes of the tumor and the surrounding site serving as comparison targets. For example, the relative relationship calculating unit 143 calculates, as shown in FIG. 4, an amplitude "ΔdA" and a cycle "TA" of the periodical distance change of the tumor and an amplitude "ΔdB" and a cycle "TB" of the periodical distance change of the surrounding site. In this manner, the relative relationship calculating unit 143 calculates an amplitude and a cycle, for each of the voxels representing the tumor and each of the voxels representing the surrounding site.

After that, the relative relationship calculating unit 143 calculates, for example, an average value of the amplitudes and an average value of the cycles of the voxels representing the tumor, as well as an average value of the amplitudes and an average value of the cycles of the voxels representing the surrounding site. Further, the relative relationship calculating unit 143 compares the average amplitude and the average cycle of the tumor with the average amplitude and the average cycle of the surrounding site. The relative relationship calculating unit 143 makes a judgment in such a manner that the larger difference there is between the average amplitudes and the average cycles, the more the tumor has infiltrated into the predetermined surrounding site, i.e., the higher is the calculated infiltration degree of the tumor. On the contrary, the relative relationship calculating unit 143 makes a judgment in such a manner that the larger similarity there is between the average amplitude and the average cycle of the tumor and the average amplitude and the average cycle of the surrounding site, the less the tumor has infiltrated into the predetermined surrounding site, i.e., the lower is the calculated infiltration degree of the tumor.

After that, the relative relationship calculating unit 143 performs the same process with respect to each of the x-, y-, and the z-axis directions so as to calculate the infiltration degree of each of the voxels, based on the infiltration degrees calculated with respect to all the directions. For example, the relative relationship calculating unit 143 uses either an average value or a maximum value of the infiltration degrees calculated with respect to all the directions, as the infiltration degree of a voxel.

It should be noted, however, that the process performed by the relative relationship calculating unit 143 is not limited to the example described above. Some of other examples of processes performed by the relative relationship calculating unit 143 will be explained below. For example, the relative relationship calculating unit 143 calculates an average value of the amplitudes and an average value of the cycles of the voxels representing the tumor. Further, the relative relationship calculating unit 143 compares the average amplitude and the average cycle of the tumor with the amplitude and the cycle of each of the voxels representing the surrounding site. In this situation, the relative relationship calculating unit 143 makes a judgment in such a manner that the larger similarity there is between the amplitude and the cycle of each of the voxels representing the surrounding site and the average amplitude and the average cycle of the tumor, the more the tumor has infiltrated into the region of the surrounding site represented by the voxel, i.e., the higher is the calculated infiltration degree of the voxel. On the contrary, the relative relationship calculating unit 143 makes a judgment in such a manner that the larger difference there is between the amplitude and the cycle of each of the voxels and the average amplitude and the average cycle of the tumor, the less the tumor has infiltrated into the region of the surrounding site represented by the voxel, i.e., the lower is the calculated infiltration degree of the voxel.

For example, in the example shown in FIG. 3, to calculate an infiltration degree of the tumor A1 into the surrounding site B1, it is possible for the relative relationship calculating unit 143 to calculate the infiltration degree in such a manner that, within the surrounding site B1, the closer a region is positioned to the tumor A1, the higher is the infiltration degree and in such a manner that the more distant a region is positioned from the tumor A1, the lower is the infiltration degree.

In another example, it is also acceptable to configure the relative relationship calculating unit 143 so as to calculate an infiltration degree of the tumor into the surrounding site B1, by using only the voxels representing the surrounding site B1. For instance, within a single surrounding site, e.g., the surrounding site B1, movements of a region positioned close to the tumor are different from movements of a region positioned distant from the tumor. The reason is that the region into which the tumor has started to infiltrate begins to get stiff and thus begins having movements that are different from those of the regions into which the tumor has not infiltrated. Accordingly, the relative relationship calculating unit 143 is able to calculate the infiltration degree by comparing the distance changes of the voxels within the single surrounding site, i.e., the surrounding site B1. For example, the relative relationship calculating unit 143 calculates an average amplitude and an average cycle of a plurality of voxels representing the surrounding site B1, and also, calculates standard deviations of the amplitude and the cycle for each of the voxels representing the surrounding site B1. If the calculated standard deviation is outside a predetermined threshold range, the relative relationship calculating unit 143 calculates the infiltration degree of the voxel to be high.

In yet another example, to calculate an infiltration degree of the tumor A1 into the surrounding site A2, it is acceptable to configure the relative relationship calculating unit 143 so as to calculate the infiltration degree by using a phase difference ("Δt" shown in FIG. 4) between the periodical distance change of the tumor and the periodical distance change of the surrounding site B1. More specifically, the relative relationship calculating unit 143 calculates the infiltration degree in such a manner that the larger the phase difference is from the surrounding site B1, the higher is the infiltration degree of the tumor into the surrounding site A2, and in such a manner that the smaller the phase difference is from the surrounding site B1, the lower is the infiltration degree of the tumor into the surrounding site A2.

In yet another example, if the surrounding site used for calculating an infiltration degree is a symmetrical site, it is also acceptable to configure the relative relationship calculating unit 143 to normalize the motion vectors of the voxels representing the surrounding site, by using the motion vectors of the voxels representing the contralateral site. This feature will be further explained, while using a lung field, which is a symmetrical site, as an example. Within a lung field, a region positioned near the diaphragm has a larger movement amount than a region in the lung apex. Accordingly, even if no tumor has infiltrated into the lung field, there is a possibility that mutually-different infiltration degrees may be calculated for the region positioned near the diaphragm and for the region in the lung apex, due to the mutually-different movement amounts (amplitudes).

To cope with this situation, when the right lung field is used as a surrounding site for calculating an infiltration degree, for instance, the relative relationship calculating unit 143 calculates motion vectors of the voxels representing the left lung field and further calculates, while using the calculated motion vectors, correction coefficients that make the amplitude of the region positioned near the diaphragm equal to the amplitude of the region in the lung apex. For example, the relative relationship calculating unit 143 calculates such a correction coefficient that makes the movement amount smaller for the region positioned near the diaphragm of which the movement amount is larger, and calculates such a correction coefficient that makes the movement amount larger for the region in the lung apex of which the movement amount is smaller.

Further, the relative relationship calculating unit 143 normalizes the movement amounts of the voxels representing the right lung field by using the calculated correction coefficients. As a result, the relative relationship calculating unit 143 is able to calculate an accurate infiltration degree. Alternatively, it is acceptable to configure the relative relationship calculating unit 143 so as to perform the normalizing process, after estimating the movement amounts of the sites (i.e., the region positioned near the diaphragm and the region in the lung apex), based on a propagation of the movements from the region positioned near the diaphragm to the region in the lung apex.

Next, the reason why the correction coefficients are calculated by using the left lung field, which is the contralateral site, will be explained. Generally speaking, the right lung field and the left lung field are considered to have the same movements as each other. In addition, generally speaking, it is safe to say that there is almost no possibility that a tumor can occur in mutually the same positions in both the right lung field and the left lung field at the same time. For this reason, the relative relationship calculating unit 143 calculates the correction coefficients by using the motion vectors of the left lung field, which is considered to be healthy. When the motion vectors of the right lung field are normalized by using the correction coefficients calculated in this manner, the sizes of the motion vectors in the regions of the right lung field are supposed to be substantially equal, if the right lung field is healthy. On the contrary, if a tumor has started to infiltrate into a region, the region has a different movement than that of the healthy region. For this reason, by making a comparison with the normalized motion vectors in the regions of the right lung field, it is possible to accurately calculate the region into which the tumor has started to infiltrate.

Further, the relative relationship calculating unit 143 generates an X-ray CT image expressing levels of the calculated infiltration degree and exercises control so that the generated image is displayed on the display unit 120. For example, the relative relationship calculating unit 143 generates a functional map from the amplitudes and the cycles of the voxels and further generates the X-ray CT image to which a gray scale or a color scale corresponding to the amplitudes and the cycles is applied.

Figure 5:
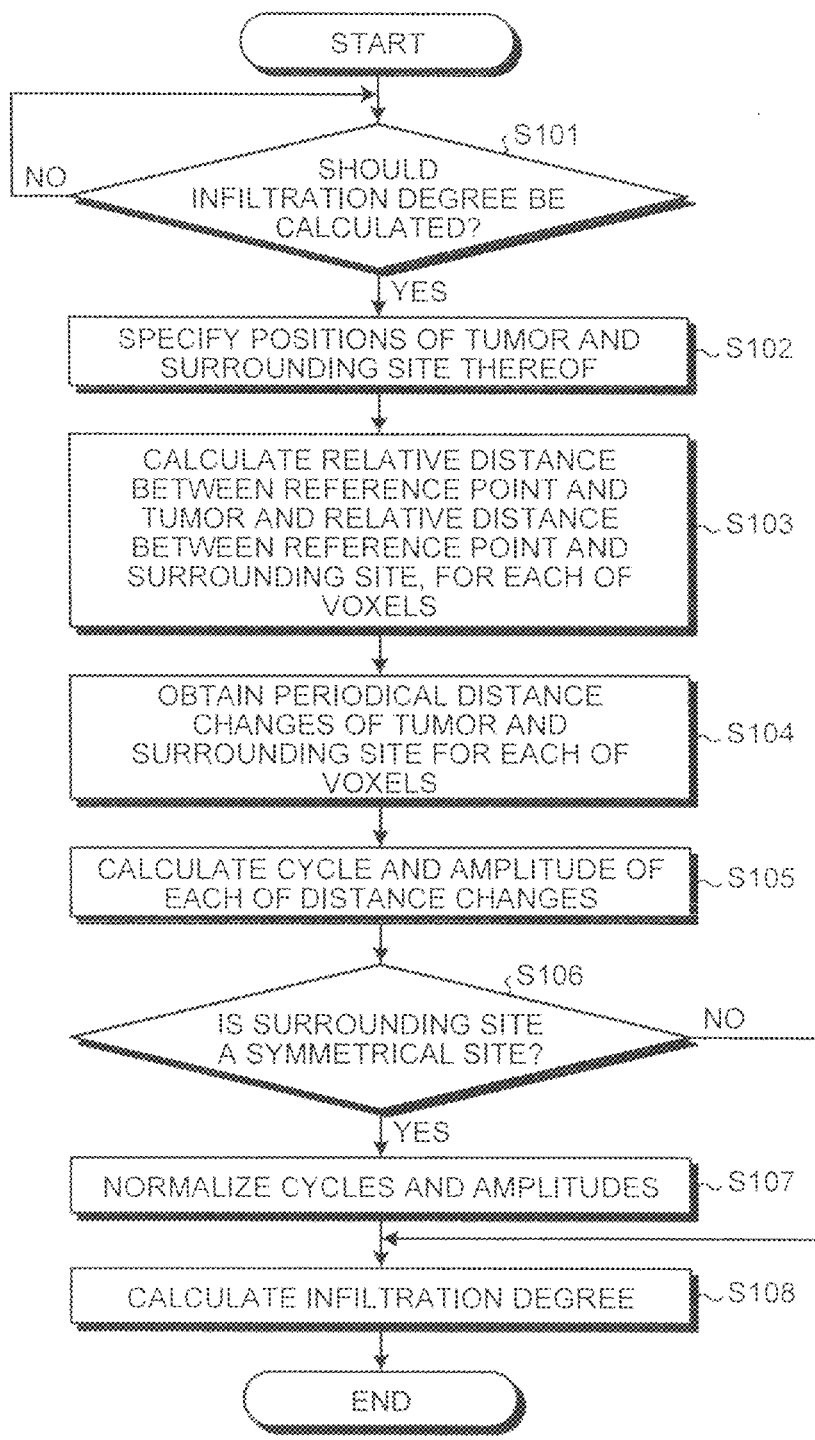
FIG. 5 is a flowchart of a procedure in an infiltration degree calculating process performed by the X-ray CT apparatus according to the first embodiment.

Next, a procedure in the infiltration degree calculating process performed by the X-ray CT apparatus 1 according to the first embodiment will be explained, with reference to FIG. 5. FIG. 5 is a flowchart of the procedure in the infiltration degree calculating process performed by the X-ray CT apparatus 1 according to the first embodiment.

As shown in FIG. 5, the image processing unit 140 included in the X-ray CT apparatus 1 judges whether an infiltration degree should be calculated (step S101). For example, the image processing unit 140 judges whether the operator has performed, via the input unit 110, an operation indicating that an infiltration degree should be calculated. In this situation, if an infiltration degree is not to be calculated (step S101: No), the image processing unit 140 goes into a standby state. Also, if it is determined in advance that an infiltration degree should be calculated, the image processing unit 140 does not need to perform the process at step S101.

On the contrary, if an infiltration degree should be calculated (step S101: Yes), the specifying unit 141 included in the image processing unit 140 specifies the position of a tumor and the position of a surrounding site of the tumor, within the volume data (step S102).

Subsequently, every time volume data is reconstructed, the movement information calculating unit 142 calculates, for each of the voxels, a relative distance from a reference point to the tumor and a relative distance from the reference point to the surrounding site (step S103) and calculates a periodical distance change of each of the voxels by comparing pieces of volume data corresponding to mutually-different temporal phases (step S104).

After that, the relative relationship calculating unit 143 calculates amplitudes, cycles, and the like with respect to the periodical distance changes of the tumor and the surrounding site serving as the comparison targets (step S105). In this situation, if the surrounding site is a symmetrical site (step S106: Yes), the relative relationship calculating unit 143 normalizes the amplitudes and the cycles of the surrounding site by using the motion vectors of the voxels representing the contralateral site thereof (step S107).

Further, by using the amplitudes and the phases calculated at step S107, the relative relationship calculating unit 143 calculates an infiltration degree by making a comparison to obtain a degree of similarity between the periodical distance changes of the voxels representing the tumor and the periodical distance changes of the voxels representing the surrounding site of the tumor (step S108).

As explained above, according to the first embodiment, the specifying unit 141 specifies the position of the tumor and the position of the surrounding site positioned in the surrounding of the tumor, from the pieces of volume data of the inside of the patient corresponding to the mutually-different temporal phases. Based on the positions of the tumor and the surrounding site specified by the specifying unit 141, the movement information calculating unit 142 calculates the movement information related to the movements of the tumor and the surrounding site. Based on the relationship between the movement information of the tumor and the movement information of the surrounding site calculated by the movement information calculating unit 142, the relative relationship calculating unit 143 calculates the infiltration degree indicating the degree by which the tumor has infiltrated into the surrounding site, as the information expressing the relationship between the tumor, which is a lesion, and the surrounding site of the tumor. Consequently, it is possible to present an objective infiltration degree of the tumor.

For instance, in the examples shown in FIG. 3, a person such as the operator might be able to determine an infiltration degree of the tumor A1 by visually comparing the X-ray CT images G11 to G14 with one another; however, it would be difficult for a person to specifically observe regions having mutually-different movements by only looking at the X-ray images G11 to G14, and the person would only be able to determine a subjective infiltration degree. In contrast, the X-ray CT apparatus 1 described above is able to calculate the objective infiltration degree of the tumor, by comparing the movements of the tumor and the surrounding site with each other.

In the first embodiment, the example is explained in which the infiltration degree of the tumor is calculated by using the amplitudes, the cycles, and the like of the periodical distance changes; however, it is also acceptable to calculate an infiltration degree of a tumor, based on a temporal change in the distance between the tumor and the surrounding site. This feature will be explained more specifically. It is assumed that, the more the tumor has infiltrated into the surrounding site, the more the tumor becomes integrated with the surrounding site, i.e., the smaller the change is in the distance between the tumor and the surrounding site. On the contrary, it is assumed that, the less the tumor has infiltrated into the surrounding site, the easier it is for the tumor to come off the surrounding site, i.e., the larger is the change in the distance between the tumor and the surrounding site that is caused by the movements of the surrounding site.

For this reason, for example, the movement information calculating unit 142 calculates a temporal change in the distance between the gravity point of the tumor and the surrounding site, as the movement information. Further, the relative relationship calculating unit 143 calculates the an infiltration degree in such a manner that the smaller the change is in the distance between the gravity point of the tumor and the surrounding site calculated by the movement information calculating unit 142 over a predetermined period of time (e.g., a respiratory cycle), the higher is the infiltration degree of the tumor into the surrounding site, and in such manner that the larger the change is in the distance between the gravity point of the tumor and the surrounding site over the predetermined period of time, the lower is the infiltration degree of the tumor into the surrounding site.

Figure 6:
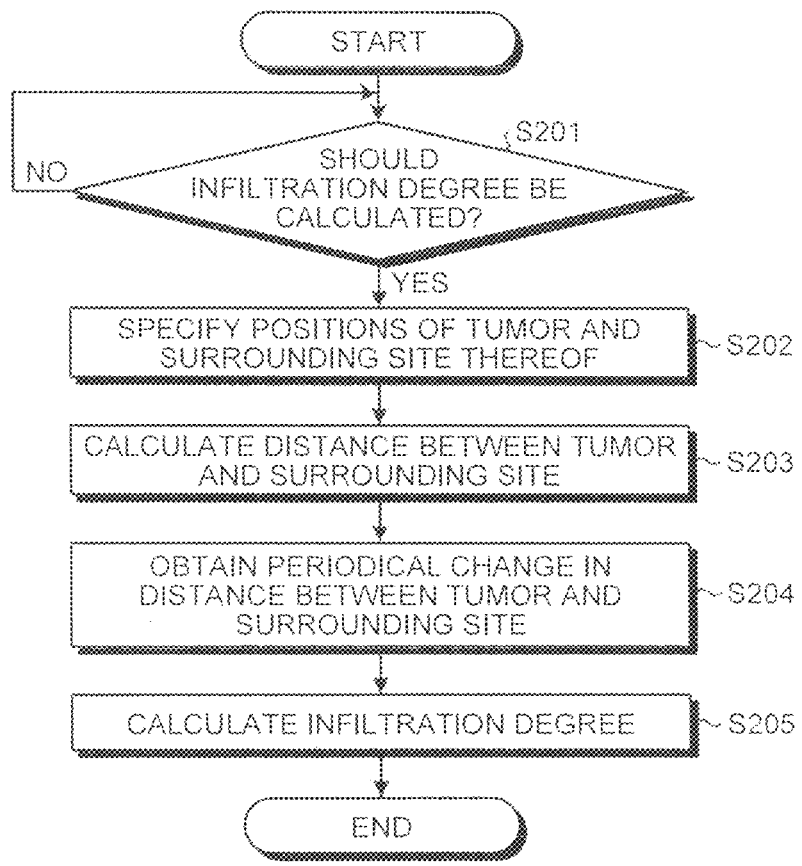
FIG. 6 is a flowchart of a procedure in another infiltration degree calculating process performed by the X-ray CT apparatus according to the first embodiment.

In FIG. 6, a procedure in the infiltration degree calculating process in the example described above is shown. As shown in FIG. 6, if an infiltration degree should be calculated (step S201: Yes), the specifying unit 141 specifies the position of a tumor and the position of a surrounding site of the tumor, within the volume data (step S202). Subsequently, every time volume data is reconstructed, the movement information calculating unit 142 calculates a distance between the gravity point of the tumor and the surrounding site (step S203) and further calculates a periodical temporal change in the distance between the gravity point of the tumor and the surrounding site, by comparing pieces of volume data corresponding to mutually-different temporal phases (step S204). Further, based on the change amount in the distance between the gravity point of the tumor and the surrounding site, the relative relationship calculating unit 143 calculates an infiltration degree of the tumor into the surrounding site (step S205).

In the example described above, it is acceptable to configure the movement information calculating unit 142 so as to normalize the maximum change amount in the distance between the gravity point of the tumor and the surrounding site, by using the maximum movement amount of the surrounding site over a predetermined period of time (e.g., a respiratory cycle). More specifically, in some situations, the size of an adhesion surface of a tumor may change in conjunction with movements of a surrounding site. For example, in some situations, the larger the movement amount of a surrounding site is, the larger is the change amount in the size of the adhesion surface of the tumor adhering to the surrounding site. In those situations, the distance between the gravity point of the tumor and the surrounding site may change in conjunction with the movements of the surrounding site, regardless of the infiltration degree of the tumor. To cope with these situations, it is acceptable to configure the movement information calculating unit 142 so as to calculate the maximum movement amount of the surrounding site and to normalize the maximum change amount in such a manner that the larger the maximum movement amount is, the smaller is the maximum change amount in the distance between the gravity point of the tumor and the surrounding site and in such a manner that the smaller the maximum movement amount is, the larger is the maximum change amount in the distance between the gravity point of the tumor and the surround site.

In the example described above, it is also acceptable to configure the movement information calculating unit 142 so as to calculate an infiltration degree of the tumor by comparing the maximum distance between the gravity point of the tumor and the surface of the surrounding site with the maximum radius of the tumor. For example, if the maximum radius of the tumor is larger than the maximum distance between the gravity point of the tumor and the surface of the surrounding site, it means that the tumor has entered the surrounding site. In that situation, the infiltration degree of the tumor is considered to be high. Accordingly, it is acceptable to configure the movement information calculating unit 142 so as to calculate the infiltration degree of the tumor, based on a ratio between the maximum distance from the gravity point of the tumor to the surface of the surrounding side and the maximum radius of the tumor.

Further, in the first embodiment described above, after performing the process of calculating the relative relationship between the movement information of the tumor and the movement information of the surrounding site, the relative relationship calculating unit 143 does not necessarily have to perform the process of calculating the infiltration degree of the tumor based on the calculated relative relationship. Further, for example, it is acceptable to configure the relative relationship calculating unit 143 to exercise control so that information indicating the relative relationship between the movement information of the tumor and the movement information of the surrounding site is displayed on the display unit 120. In this example also, the operator is able to determine an objective infiltration degree of the tumor, by observing the relative relationship displayed on the display unit 120.

In the above-described examples, a case has been explained in which the relative relationship calculating unit 143 calculates an infiltration degree based on a relative relationship between the movement information of the tumor and the movement information of the surrounding site. However, embodiments are not limited to this situation. For example, the relative relationship obtained in this way for the purpose of evaluating the infiltration degree in the first embodiment can be utilized to evaluate quantities other than the infiltration degree, such as estimating a degree of coupling by which the tumor and the surrounding site are coupled. As an example of the degree of coupling, the degree of coupling is a value representing a degree of adhesion (or degree of conglutination) of the tumor to the surrounding site. Needless to say, the degree of coupling is a more general concept than the infiltration degree, hence the infiltration degree is subsumed into the degree of coupling by its definition.

In this situation, for example, the generating unit 11 generates pieces of image data of an inside of a patient corresponding to mutually-different temporal phases, based on X-rays having transmitted through the patient. The specifying unit 141 specifies a position of a tumor and a position of a surrounding site positioned in a surrounding of the tumor, from the generated pieces of image data of the inside of the patient corresponding to the mutually-different temporal phases. The movement information calculating unit 142 calculates movement information related to movements of the tumor and the surrounding site, based on the specified positions of the tumor and the surrounding site. The relative relationship calculating unit 143 calculates a relative relationship between the calculated movement information of the tumor and the surrounding site. The relative relationship calculating unit 143 calculates a degree of coupling by which the tumor and the surrounding site are coupled, based on a relative relationship between the movement information of the tumor and the surrounding site.

As a specific example, the movement information calculating unit 142 calculates, for each of regions in the surrounding site, movement information of the region. In this situation the relative relationship calculating unit 143 calculates, for each of the regions, a degree of coupling by which the tumor and the surrounding site are coupled, based on a relationship between the calculated movement information and the calculated movement information of the tumor.

Alternatively, the movement information calculating unit 142 calculates a periodical positional change of the tumor and the surrounding site, as the movement information. In this situation, the relative relationship calculating unit 143 calculates the degree of coupling, based on a degree of similarity between the calculated periodical positional change of the tumor and the surrounding site. For example, the relative relationship calculating unit 143 determines the degree of similarity between the positional changes of the tumor and the surrounding site, based on at least one of an amplitude difference, a cycle difference, and a phase difference between the calculated periodical positional change of the tumor and the surrounding site.

Alternatively, the movement information calculating unit 142 calculates a distance between a gravity point of the tumor and a surrounding site to which the tumor is adhering, as the movement information. The relative relationship calculating unit 143 calculates the degree of coupling, based on a temporal change in the distance between the gravity point of the tumor and the surrounding site.

Alternatively, when the surrounding site is a symmetrical site that is substantially bilaterally symmetrical in a human body, the movement information calculating unit 142 calculates movement information of a contralateral site positioned opposite to the surrounding site. The relative relationship calculating unit 143 calculates the degree of coupling after normalizing the movement information of the surrounding site, by using the calculated movement information of the contralateral site.

Further, the first embodiment is explained above while using the tumor as an example of a lesion; however, it is acceptable to configure the X-ray CT apparatus 1 to calculate information indicating a relationship between a lesion other than a tumor and a surrounding site thereof. In the following sections, an example will be explained in which a degree of close adhesion (hereinafter, "close-adhesion degree") by which blood clots are closely adhering to a blood vessel is calculated.

First, the specifying unit 141 extracts regions by performing a segmentation process while applying a region growing method or a pattern matching method that uses shape templates, to the pieces of volume data reconstructed by the image processing unit 140. The specifying unit 141 further specifies the positions of the blood vessel and the blood clots contained in the volume data, by applying, for example, a pattern matching method that uses shape templates of a blood vessel and blood clots or a method that uses profiles of brightness values of a blood vessel and blood clots, to the extracted regions. Further, based on the positions of the blood vessel and the blood clots specified by the specifying unit 141, the movement information calculating unit 142 calculates movement information of the blood vessel and the blood clots.

After that, the relative relationship calculating unit 143 calculates a relative relationship between the movement information of the blood vessel and the movement information of the blood clots calculated by the movement information calculating unit 142 and further calculates a close-adhesion degree by which the blood clots are closely adhering to the blood vessel, based on the calculated relative relationship. For example, the relative relationship calculating unit 143 calculates the close-adhesion degree in such a manner that the larger similarity there is between the movement information of the blood vessel and the movement information of the blood clots, the higher is the close-adhesion degree of the blood clots to the blood vessel and in such a manner that the smaller similarity there is between the movement information of the blood vessel and the movement information of the blood clots, the lower is the close-adhesion degree of the blood clots to the blood vessel. As a result, the X-ray CT apparatus 1 according to the first embodiment is able to present the close-adhesion degree of the blood clots to the blood vessel based on the movement information of the blood vessel and the blood clots, in other words, an index value indicating whether it is easy for the blood clots to come off the blood vessel.

Second Embodiment

In the first embodiment above, the example is explained in which the infiltration degree of the tumor is calculated based on the movement information of the tumor and the surrounding site thereof. In a second embodiment, an example will be explained in which an infiltration degree of a tumor is calculated based on an adhesion area of the tumor and a surrounding site thereof.

Figure 7:
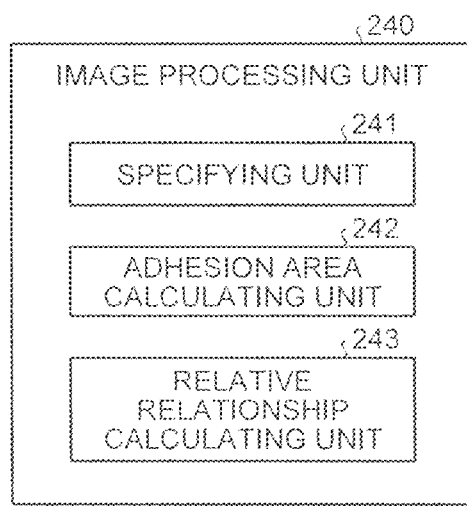
FIG. 7 is a diagram of an exemplary configuration of an image processing unit according to a second embodiment.

FIG. 7 is a diagram of an exemplary configuration of an image processing unit 240 according to the second embodiment. The configuration of an X-ray CT apparatus according to the second embodiment is similar to that of the X-ray CT apparatus 1 shown in FIG. 1; thus, the explanation thereof will be omitted. As shown in FIG. 7, the image processing unit 240 includes a specifying unit 241, an adhesion area calculating unit 242, and a relative relationship calculating unit 243.

The specifying unit 241 specifies a tumor and a surrounding site to which the tumor is presumed to be adhering, within volume data reconstructed by the image processing unit 240. The specifying unit 241 performs the same process on each of the pieces of volume data corresponding to temporal phases. Like the specifying unit 141, the specifying unit 241 extracts regions by performing the segmentation process or the like and specifies the positions of the tumor and the surrounding site thereof contained in the volume data, by using a pattern matching method or the like.

The adhesion area calculating unit 242 calculates, for each of temporal phases, an adhesion area size of the surface by which the tumor specified by the specifying unit 241 is adhering to the surrounding site. For example, based on a result of the segmentation process performed by the specifying unit 241, the adhesion area calculating unit 242 is able to obtain a surface image of the tumor and a surface image of the surrounding site to which the tumor is adhering. Further, the adhesion area calculating unit 242 is able to calculate a shared region between the surface image of the tumor and the surface image of the surrounding site, as the adhesion area of the surface by which the tumor is adhering to the surrounding site.

In another example where, for instance, a tumor is adhering to a lung field, the adhesion area calculating unit 242 is able to obtain volume data of the lung field from which the tumor is missing, as a result of the segmentation process or the like performed by the specifying unit 241. Accordingly, the adhesion area calculating unit 242 is able to calculate the region rendered as a hollow in the volume data, as the adhesion area by which the tumor is adhering to the lung field. This method may be used for calculating an adhesion area between, for example, the chest wall, the mediastinum, or the diaphragm, and the tumor.

The relative relationship calculating unit 243 calculates an infiltration degree in such a manner that the smaller the change amount is in the adhesion area calculated by the adhesion area calculating unit 242, the higher is the infiltration degree of the tumor into the surrounding site and in such a manner that the larger the change amount is in the adhesion area, the lower is the infiltration degree of the tumor into the surrounding site.

Figure 8:
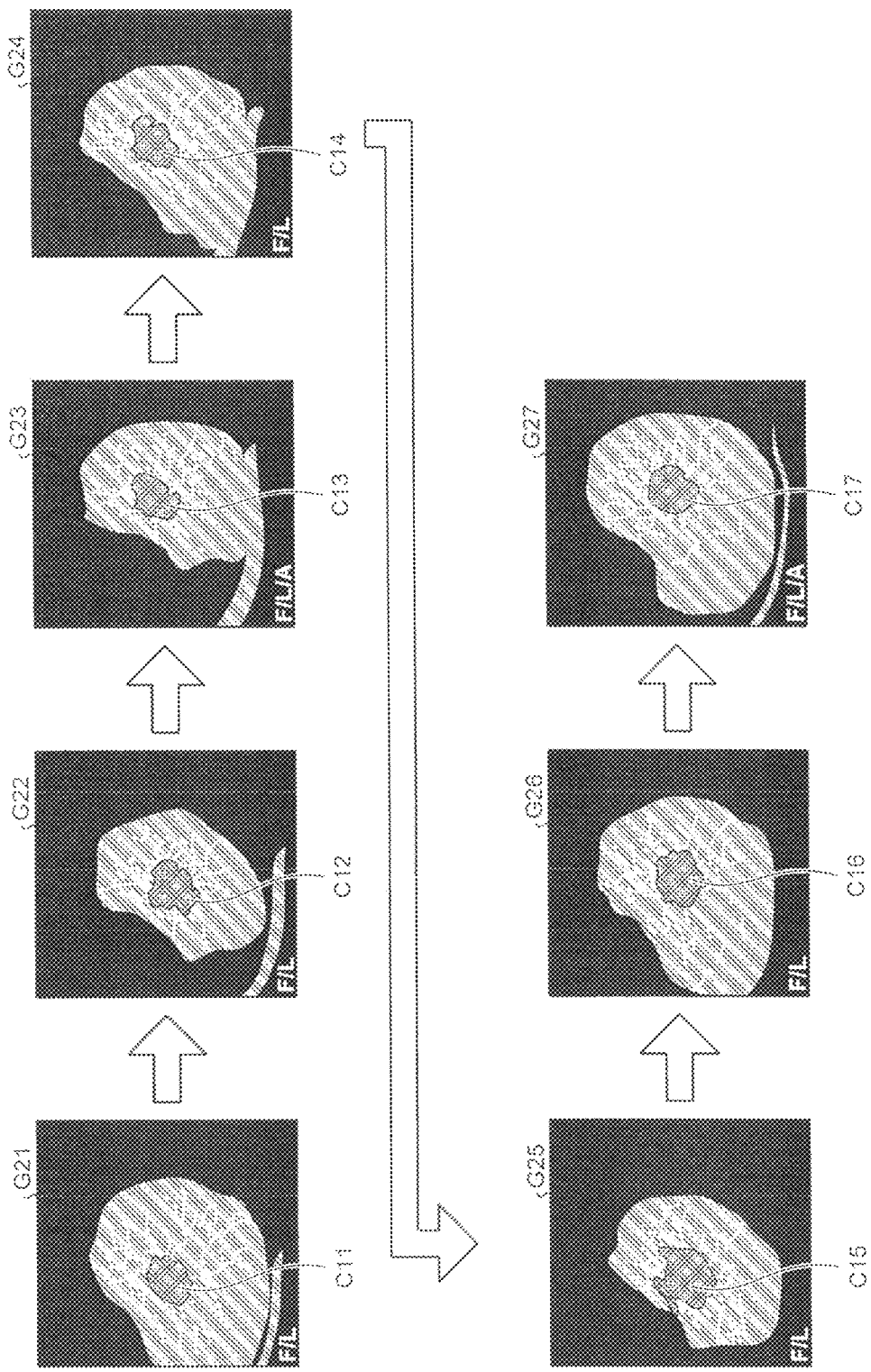
FIG. 8 depicts examples of adhesion areas between a tumor and a lung field.
Figure 9:
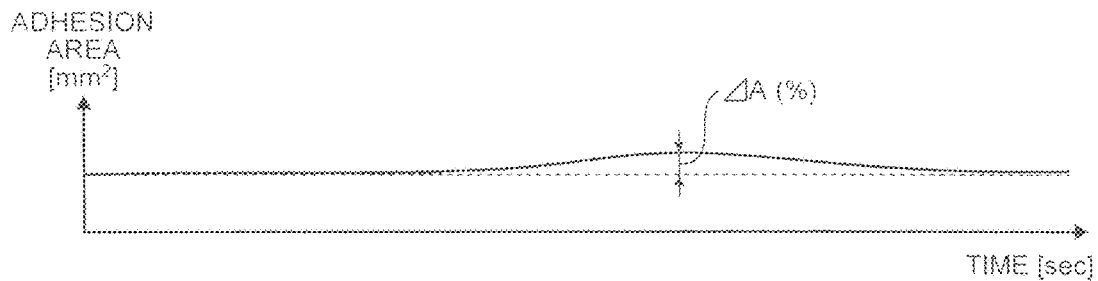
FIG. 9 is a chart of an example of a change amount in the adhesion area.

Next, an example of the process performed by the relative relationship calculating unit 243 will be explained, with reference to FIGS. 8 and 9. FIG. 8 depicts examples of adhesion areas between a tumor and a lung field. FIG. 9 is a chart of an example of a change amount in the adhesion area.

In the examples shown in FIG. 8, it is assumed that X-ray CT images G21, G22, G23, G24, G25, G26, and G27 were sequentially taken in the stated order. In FIG. 8, cross-sectional images are shown, to keep the explanation simple.

When the X-ray CT images G21 to G27 shown in FIG. 8 have been taken, the adhesion area calculating unit 242 calculates a shared region between the surface image of the tumor and the surface image of the surrounding site, as an adhesion area of the surface by which the tumor is adhering to the surrounding site. In the present example, as shown in FIG. 8, the adhesion area calculating unit 242 calculates adhesion areas C11 to C17.

Further, as shown in FIG. 9, the relative relationship calculating unit 243 obtains a temporal change in the adhesion area by plotting the adhesion areas calculated by the adhesion area calculating unit 242 along a time series. Further, the relative relationship calculating unit 243 calculates a maximum change amount ΔA in the adhesion area over a predetermined period of time (e.g., a respiratory cycle) so as to calculate an infiltration degree in such a manner that the smaller the calculated maximum change amount ΔA is, the higher is the infiltration degree of the tumor into the surrounding site, and in such a manner that the larger the maximum change amount ΔA is, the lower is the infiltration degree of the tumor into the surrounding site.

Figure 10:
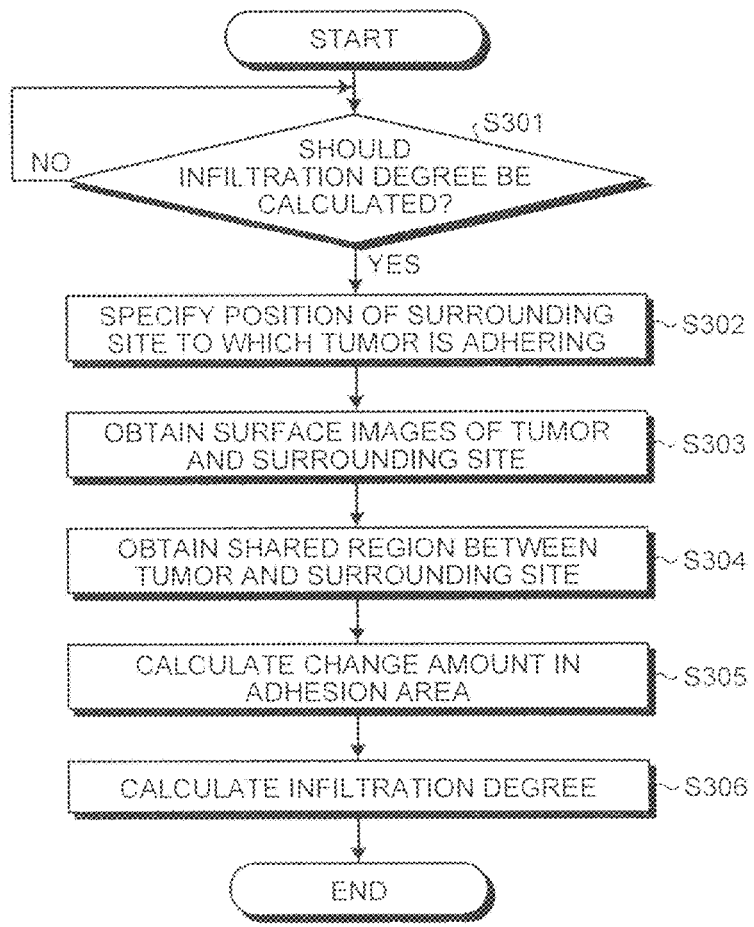
FIG. 10 is a flowchart of a procedure in an infiltration degree calculating process performed by an X-ray CT apparatus according to the second embodiment.

Next, a procedure in the infiltration degree calculating process performed by the X-ray CT apparatus according to the second embodiment will be explained, with reference to FIG. 10. FIG. 10 is a flowchart of the procedure in the infiltration degree calculating process performed by the X-ray CT apparatus according to the second embodiment.

As shown in FIG. 10, the image processing unit 240 judges whether an infiltration degree should be calculated (step S301). In this situation, if an infiltration degree is not to be calculated (step S301: No), the image processing unit 240 goes into a standby state.

On the contrary, if an infiltration degree should be calculated (step S301: Yes), the specifying unit 241 included in the image processing unit 240 specifies a tumor and a surrounding site to which the tumor is presumed to be adhering, within the volume data (step S302).

Subsequently, the adhesion area calculating unit 242 obtains surface images of the tumor and the surrounding site, based on a result of the segmentation process performed by the specifying unit 241 (step S303). Further, the adhesion area calculating unit 242 obtains a shared region between the surface image of the tumor and the surface image of the surrounding site (step S304). Thus, the adhesion area calculating unit 242 calculates an adhesion area of the surface by which the tumor is adhering to the surrounding site, by calculating the area size of the shared region.

Subsequently, the relative relationship calculating unit 243 calculates a change amount in the adhesion area calculated by the adhesion area calculating unit 242 over a predetermined period of time (step S305). After that, based on the change amount in the adhesion area, the relative relationship calculating unit 243 calculates an infiltration degree of the tumor into the surrounding site (step S306).

As explained above, according to the second embodiment, the specifying unit 241 specifies the position of the tumor and the position of the surrounding site to which the tumor is presumed to be adhering, from the pieces of image data of the inside of the patient corresponding to the mutually-different temporal phases. For each of the temporal phases, the adhesion area calculating unit 242 calculates the adhesion area of the surface by which the tumor specified by the specifying unit 241 is adhering to the surrounding site. The relative relationship calculating unit 243 calculates the infiltration degree indicating the degree by which the tumor has infiltrated into the surrounding site in such a manner that the smaller the change amount is in the adhesion area calculated by the adhesion area calculating unit 242, the higher is the infiltration degree. Consequently, only by calculating the adhesion areas, it is possible to present an objective infiltration degree of the tumor.

In the second embodiment a case has been explained in which the adhesion area calculation unit 242 calculates an adhesion area of the tumor and the relative relationship calculating unit 243 calculates an infiltration degree of a tumor based on the adhesion area calculated by the adhesion area calculation unit 242. However, embodiments are not limited to this situation. In other words, the relative relationship calculating unit 243 may calculate values other than the infiltration degree. For example, the relative relationship calculating unit 243 may calculate a degree of coupling by which the lesion and the surrounding site are coupled.

An example of the degree of coupling includes the infiltration degree as well as other quantity such as a degree of adhesion (or degree of conglutination). In other words, the relative relationship calculating unit 243 may calculate a value representing a degree of adhesion of the lesion to the surrounding site based on the adhesion area calculated by the adhesion area calculating unit 242.

Alternatively, the relative relationship calculating unit 243 may calculate the degree of coupling by calculating an infiltration degree indicating a degree by which a tumor serving as the lesion has infiltrated into the surrounding site in such a manner that the smaller a change amount is in the adhesion area by which the tumor is adhering to the surrounding site and that was calculated by the adhesion are calculating unit, the higher is the infiltration degree.

The second embodiment is explained above while using the tumor as an example of a lesion; however, it is acceptable to configure the X-ray CT apparatus according to the second embodiment to calculate information indicating a relationship between a lesion other than a tumor and a surrounding site thereof. In the following sections, an example will be explained in which a close-adhesion degree by which blood clots are closely adhering to a blood vessel is calculated.

First, like the specifying unit 141, the specifying unit 241 specifies the positions of the blood vessel and the blood clots contained in the volume data by performing the segmentation process or the like. Further, based on a result of the segmentation process performed by the specifying unit 241, for example, the adhesion area calculating unit 242 calculates a shared region between the surface image of the blood vessel and the surface image of the blood clots, as an adhesion area of the surface by which the blood clots are adhering to the blood vessel. Further, the relative relationship calculating unit 243 calculates a close-adhesion degree in such a manner that the smaller the change amount is in the adhesion area calculated by the adhesion area calculating unit 242, the higher is the close-adhesion degree of the blood clots to the blood vessel, and in such a manner that the larger the change amount is in the adhesion area, the lower is the close-adhesion degree of the blood clots to the blood vessel. As a result, the X-ray CT apparatus according to the second embodiment is able to present the close-adhesion degree of the blood clots to the blood vessel based on the change amount in the adhesion area between the blood vessel and the blood clots, in other words, an index value indicating whether it is easy for the blood clots to come off the blood vessel.

In the exemplary embodiments described above, the example is explained in which the X-ray CT apparatus displays the X-ray CT image expressing the levels of the infiltration degree on the display unit 120. However, it is also acceptable to configure the X-ray CT apparatus to exercise control so that the display unit 120 displays not only the X-ray CT image, but also the movement information calculated by the movement information calculating unit 142 (FIG. 4 and so on), the information related to the adhesion area calculated by the adhesion area calculating unit 242, the infiltration degree, and the like. Further, it is acceptable to configure the X-ray CT apparatus to store these various types of information into a predetermined storage unit.

Further, in the exemplary embodiments described above, the example is explained in which the X-ray CT apparatus specifies the positions of the tumor and the surrounding site by performing the information processing process that employs, for example, the pattern matching method. In that example, it is acceptable to configure the X-ray CT apparatus to receive an operation of designating the positions of the tumor and the surrounding site from the operator via the input unit 110, after displaying the X-ray CT image on the display unit 120. In that situation, the X-ray CT apparatus specifies the positions of the tumor and the surrounding site, according to the designating operation of the operator.

Further, in the exemplary embodiments described above, the example is explained in which the X-ray CT apparatus calculates the movement information by comparing two consecutive pieces of volume data with each other at appropriate times. The X-ray CT apparatus, however, does not necessarily have to perform the process on all the pieces of volume data. It is acceptable to configure the X-ray CT apparatus so as to calculate the movement information after thinning the volume data serving as the processing target.

Further, in the exemplary embodiments described above, the example is explained in which the X-ray CT apparatus calculates the movement information by using the volume data; however, it is acceptable to configure the X-ray CT apparatus so as to calculate an infiltration degree of the tumor by calculating movement information, while using two-dimensional image data.

Further, in the exemplary embodiments described above, the example is explained in which the X-ray CT apparatus performs the conventional scanning process; however, the exemplary embodiments described above are also applicable to an X-ray CT apparatus configured to perform a helical scanning process by which it is possible to reconstruct volume data in correspondence with multiple temporal phases.

Furthermore, the exemplary embodiments described above are also applicable to an X-ray CT apparatus that is not capable of performing an image taking process corresponding to temporal phases that are sufficient, in quantity, to provide the periodical information such as the distance changes. For example, it is possible to calculate an infiltration degree of a tumor by using the maximum movement amounts of the tumor and the surrounding site, as the amplitudes "Δd" explained in the first embodiment.

As explained above, according to the first and the second embodiments, it is possible to present the information indicating the relationship between the lesion and the surrounding site.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
an image processing circuit configured to
generate pieces of image data of an inside of a patient corresponding to mutually-different temporal phases, based on X-rays having transmitted through the patient;
specify a position of a tumor and a position of a surrounding site positioned in a surrounding region of the tumor, from the generated pieces of image data of the inside of the patient corresponding to the mutually-different temporal phases;
calculate movement information related to movements of the tumor and the surrounding site, based on the specified positions of the tumor and the surrounding site;
calculate a relative relationship between the calculated movement information of the tumor and the surrounding site; and
calculate a degree to which the tumor influences the surrounding site, based on the relative relationship between the movement information of the tumor and the surrounding site.

2. The X-ray CT apparatus according to claim 1, wherein the degree to which the tumor influences the surrounding site is a value representing a degree of adhesion of the tumor to the surrounding site.

3. The X-ray CT apparatus according to claim 1, wherein the image processing circuit calculates, for each of regions in the surrounding site, movement information of the region, and calculates, for each of the regions, a degree to which the tumor influences the surrounding site, based on a relationship between the calculated movement information and the calculated movement information of the tumor.

4. The X-ray CT apparatus according to claim 1, wherein the image processing circuit calculates a periodical positional change of the tumor and the surrounding site, as the movement information, and calculates the degree to which the tumor influences the surrounding site, based on a degree of similarity between the calculated periodical positional change of the tumor and the surrounding site.

5. The X-ray CT apparatus according to claim 4, wherein the image processing circuit determines the degree of similarity between the positional changes of the tumor and the surrounding site, based on at least one of an amplitude difference, a cycle difference, and a phase difference between the calculated periodical positional change of the tumor and the surrounding site.

6. The X-ray CT apparatus according to claim 1, wherein the image processing circuit calculates a distance between a gravity point of the tumor and a surrounding site to which the tumor is adhering, as the movement information, and calculates the degree to which the tumor influences the surrounding site, based on a temporal change in the distance between the gravity point of the tumor and the surrounding site.

7. The X-ray CT apparatus according to claim 1, wherein when the surrounding site is a symmetrical site that is substantially bilaterally symmetrical in a human body, the image processing circuit calculates movement information of a contralateral site positioned opposite to the surrounding site, and calculates the degree to which the tumor influences the surrounding site after normalizing the movement information of the surrounding site, by using the calculated movement information of the contralateral site.

8. The X-ray CT apparatus according to claim 1, wherein the degree to which the tumor influences the surrounding site is a degree of coupling by which the tumor and the surrounding site are coupled.

9. An image processing method, comprising:
generating, by an image processing circuit, pieces of image data of an inside of a patient corresponding to mutually-different temporal phases, based on X-rays having transmitted through the patient;
specifying, by the image processing circuit, a position of a tumor serving as a lesion and a position of a surrounding site positioned in a surrounding region of the tumor, from the generated pieces of image data of the inside of the patient corresponding to the mutually-different temporal phases;
calculating, by the image processing circuit, movement information related to movements of the tumor and the surrounding site, based on the specified position of the tumor and the surrounding site;
calculating, by the image processing circuit, a relative relationship between the movement information of the tumor and the surrounding site; and
calculating, by the image processing circuit, a degree to which the tumor influences the surrounding site, based on the relative relationship between the movement information of the tumor and the surrounding site.

10. The image processing method according to claim 9, wherein the degree to which the tumor influences the surrounding site is a value representing a degree of adhesion of the tumor to the surrounding site.

11. The image processing method according to claim 9, further comprising:
calculating, by the image processing circuit, for each of regions in the surrounding site, movement information of the region; and
calculating, by the image processing circuit, for each of the regions, a degree to which the tumor influences the surrounding site, based on a relationship between the calculated movement information of the regions and the calculated movement information of the tumor.

12. The image processing method according to claim 9, further comprising:
calculating, by the image processing circuit, a periodical positional change of the tumor and the surrounding site, as the movement information; and
calculating, by the image processing circuit, the degree to which the tumor influences the surrounding site, based on a degree of similarity between the calculated periodical positional change of the tumor and the surrounding site.

13. The image processing method according to claim 12, further comprising:
determining, by the image processing circuit, the degree of similarity between the positional changes of the tumor and the surrounding site, based on at least one of an amplitude difference, a cycle difference, and a phase difference between the calculated periodical positional change of the tumor and the surrounding site.

14. The image processing method according to claim 9, further comprising:
calculating, by the image processing circuit, a distance between a gravity point of the tumor and a surrounding site to which the tumor is adhering, as the movement information, and
calculating, by the image processing circuit, the degree to which the tumor influences the surrounding site, based on a temporal change in the distance between the gravity point of the tumor and the surrounding site.

15. The image processing method according to claim 9, further comprising:
when the surrounding site is a symmetrical site that is substantially bilaterally symmetrical in a human body,
calculating, by the image processing circuit, movement information of a contralateral site positioned opposite to the surrounding site, and
calculating, by the image processing circuit, the degree to which the tumor influences the surrounding site after normalizing the movement information of the surrounding site, by using the calculated movement information of the contralateral site.

16. The image processing method according to claim 9, wherein the degree to which the tumor influences the surrounding site is a degree of coupling by which the tumor and the surrounding site are coupled.

* * * * *